United States Patent
Sandelson (10) Patent No.: US 12,186,045 B2
(45) Date of Patent: Jan. 7, 2025

(54) SYSTEMS, DEVICES, AND METHODS FOR TRIGGERING INTRAOPERATIVE NEUROMONITORING IN ROBOTIC-ASSISTED MEDICAL PROCEDURES

(71) Applicant: Mazor Robotics Ltd., Caesarea (IL)

(72) Inventor: Adi Sandelson, Givatayim (IL)

(73) Assignee: Mazor Robotics Ltd., Caesarea (IL)

( * ) Notice: Subject to any disclaimer, the term of this patent is extended or adjusted under 35 U.S.C. 154(b) by 443 days.

(21) Appl. No.: 17/590,045

(22) Filed: Feb. 1, 2022

(65) Prior Publication Data
US 2023/0240777 A1    Aug. 3, 2023

(51) Int. Cl.
A61B 34/30   (2016.01)
A61B 5/388   (2021.01)
A61B 34/37   (2016.01)
G05B 19/4155 (2006.01)

(52) U.S. Cl.
CPC .............. *A61B 34/37* (2016.02); *A61B 5/388* (2021.01); *G05B 19/4155* (2013.01); *G05B 2219/45117* (2013.01)

(58) Field of Classification Search
CPC .... A61B 34/37; A61B 5/388; G05B 19/4155; G05B 2219/45117
See application file for complete search history.

(56) References Cited

U.S. PATENT DOCUMENTS

| | | | |
|---|---|---|---|
| 10,987,050 B2 | 4/2021 | Bonfils-Rasmussen | |
| 2008/0183074 A1 | 7/2008 | Carls et al. | |
| 2018/0092559 A1 | 4/2018 | Wybo | |
| 2018/0168564 A1 | 6/2018 | Tischendorf et al. | |
| 2019/0091472 A1* | 3/2019 | Friedenberg | A61N 1/36003 |
| 2019/0262084 A1 | 8/2019 | Roh et al. | |
| 2019/0344075 A1* | 11/2019 | Bloch | A61B 5/4839 |
| 2020/0170716 A1 | 6/2020 | Quaid, III | |
| 2021/0038326 A1 | 2/2021 | Kostrzewwski | |
| 2022/0022951 A1* | 1/2022 | Townley | G16H 20/30 |
| 2024/0148455 A1* | 5/2024 | Donovan | A61B 17/3421 |

FOREIGN PATENT DOCUMENTS

WO    WO 2021/062373    4/2021

OTHER PUBLICATIONS

International Search Report and Written Opinion for International (PCT) Patent Application No. PCT/IL2023/050054, dated Apr. 21, 2023, 17 pages.

* cited by examiner

*Primary Examiner* — Dalena Tran
(74) *Attorney, Agent, or Firm* — Sheridan Ross P.C.

(57) ABSTRACT

A system comprises a neuromonitoring system configured to generate nerve data regarding a state of a nerve of a patient during a surgical procedure on the patient. The system includes a robotic system configured to receive or generate, for the surgical procedure, location data that identifies a location of the nerve of the patient. The robotic system may cause the neuromonitoring system to be in either an active state or an inactive state based on the location data, where the active state is a state in which the neuromonitoring system provides the nerve data to the robotic system, while the inactive state is a state in which the neuromonitoring system does not provide the nerve data to the robotic system. The robotic system may further generate at least one control signal that implements one or more safeguards for the surgical procedure.

20 Claims, 4 Drawing Sheets

SYSTEMS, DEVICES, AND METHODS FOR TRIGGERING INTRAOPERATIVE NEUROMONITORING IN ROBOTIC-ASSISTED MEDICAL PROCEDURES

BACKGROUND

The present disclosure is generally directed to systems, devices, and methods for triggering intraoperative neuromonitoring in robotic-assisted medical procedures.

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following placement of a medical implant in the patient anatomy.

BRIEF SUMMARY

Example aspects of the present disclosure include:

A system, comprising: a neuromonitoring system configured to generate nerve data regarding a state of a nerve of a patient during a surgical procedure on the patient; and a robotic system configured to: receive or generate, for the surgical procedure, location data that identifies a location of the nerve of the patient; cause the neuromonitoring system to be in either an active state or an inactive state based on the location data, the active state being a state in which the neuromonitoring system provides the nerve data to the robotic system, the inactive state being a state in which the neuromonitoring system does not provide the nerve data to the robotic system; and generate at least one control signal that implements one or more safeguards for the surgical procedure.

Any of the aspects herein, wherein the robotic system is configured to generate the at least one control signal based on the nerve data.

Any of the aspects herein, wherein the robotic system is configured to generate the at least one control signal further based on the location data.

Any of the aspects herein, wherein the robotic system is configured to generate the at least one control signal based on the location data.

Any of the aspects herein, wherein the robotic system further comprises: a robotic arm, and wherein the at least one control signal causes movement of the robotic arm to stop.

Any of the aspects herein, wherein the robotic system further comprises: a robotic arm, and wherein the at least one control signal causes the robotic system to determine a new path of motion for the robotic arm.

Any of the aspects herein, wherein the robotic system further comprises: a surgical tool, and wherein the at least one control signal causes operation of the surgical tool to stop.

Any of the aspects herein, wherein the robotic system further comprises: a surgical tool, wherein the robotic system is configured to: generate tool data that identifies a current operation frequency of the surgical tool, and cause the neuromonitoring system to be in either the active state or the inactive state further based on the tool data.

Any of the aspects herein, wherein the robotic system is configured to: determine, using the location data, whether a part of the robotic system is within a threshold distance of the nerve of the patient; cause the neuromonitoring system to be in the active state when the part of the robotic system is within the threshold distance of the nerve of the patient; and cause the neuromonitoring system to be in the inactive state when the part of the robotic system is not within the threshold distance of the nerve of the patient.

Any of the aspects herein, wherein the part of the robotic system corresponds to a robotic arm or a surgical tool.

Any of the aspects herein, wherein the at least one control signal causes an audio and/or visual alert to be produced for a clinician performing the surgical procedure.

A robotic system, comprising: a robotic arm; a surgical tool mechanically coupled to the robotic arm; and processing circuitry configured to: receive or generate, for a surgical procedure on a patient, location data that identifies a location of a nerve of the patient; and cause a neuromonitoring system to be in either an active state or an inactive state based on the location data, the active state being a state in which the neuromonitoring system provides nerve data regarding a state of the nerve of the patient to the robotic system, the inactive state being a state in which the neuromonitoring system does not provide the nerve data to the robotic system.

Any of the aspects herein, wherein the processing circuitry is configured to generate at least one control signal that implements one or more safeguards for the surgical procedure.

Any of the aspects herein, wherein the processing circuitry is configured to generate the at least one control signal based on the location data or the nerve data, or based on the location data and the nerve data.

Any of the aspects herein, wherein the at least one control signal causes the robotic arm or the surgical tool to stop.

Any of the aspects herein, wherein the at least one control signal causes the robotic arm to follow a new path of motion.

Any of the aspects herein, wherein the processing circuitry is configured to: determine, using the location data, whether a part of the robotic system is within a threshold distance of the nerve of the patient; cause the neuromonitoring system to be in the active state when the part of the robotic system is within the threshold distance of the nerve of the patient; and cause the neuromonitoring system to be in the inactive state when the part of the robotic system is not within the threshold distance of the nerve of the patient.

Any of the aspects herein, wherein the part of the robotic system corresponds to the robotic arm or the surgical tool.

A method, comprising: receiving location data that identifies a location of a nerve of a patient within a robotic system that assists with a surgical procedure on the patient; determining, using the location data, whether a part of the robotic system is within a threshold distance of the nerve; causing a neuromonitoring system to be in an active state when the part of the robotic system is within the threshold distance of the nerve, the active state being a state in which the neuromonitoring system provides nerve data regarding a state of the nerve of the patient to the robotic system; and maintaining the neuromonitoring system in an inactive state when the part of the robotic system is not within the threshold distance of the nerve, the inactive state being a state in which the neuromonitoring system does not provide the nerve data to the robotic system.

Any of the aspects herein, further comprising: generating, based on the nerve data provided by the neuromonitoring system in the active state, at least one control signal that implements one or more safeguards for the surgical procedure; and mapping a no-fly zone for the part of the robotic system based on the nerve data or the location data, or both of the nerve data and the location data.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Safety and accuracy are the top goals in robotic-assisted medical procedures and development teams. During robotic-assisted surgical procedures, instrumentation can be in very close proximity to sensitive parts of a patient's nervous system such as nerves. Inventive concepts propose to synchronize data from a neuromonitoring system with the robotic system to alert the user or stop the robotic action if, for example, the tools guided by the robot are in close proximity to the nerves.

In a spinal robotic procedure, surgical instrumentation may be operated in close proximity to parts of the patient's nervous system. During spinal procedures, for example, an intraoperative neuromonitoring system is used to check for nerve damage at different stages of the procedure. In related art techniques, the surgeon issues verbal queues or commands to the neuromonitoring operator about when to turn on the neuromonitoring system to check for nerve damage. Other techniques may include an "always-on" approach where the neuromonitoring system is powered on more most or all of the procedure, thereby consuming unnecessary power. At least one example embodiment proposes to automate this step by using the data for controlling the robot. In addition, example embodiments propose to automatically take other safety precautions (e.g., alert the surgeon) in cases where the neuromonitoring system indicates that there is a risk of damage to the nerves.

At least one example embodiment proposes to place a neuromonitoring system in communication with the robotic system assisting the surgeon with the procedure. The robotic system may activate the neuromonitoring system when parts of the robotic system (e.g., a robotic arm and/or surgical tool) are in close proximity to nerves and/or when a tool (e.g., a bone saw) operates at a specific frequency (e.g., a frequency known to increase risk of nerve damage). The robotic system receives nerve data from the neuromonitoring system, analyzes the nerve data, and tailors a response to the nerve data. Responses might include but are not limited to: stopping robot movement, stopping power tool operation, alerting a user visually and/or with an audio signal, and changing robot motion plan to a different one. The data from neuromonitoring can also be used for landmarking—to map a no fly zone for the robot. As such, inventive concepts improve the safety to the patient and improve the accuracy of the surgical procedure.

As may be appreciated, embodiments of the present disclosure provide technical solutions to one or more of the problems of (1) resource intensive procedures that require manual intervention to activate and deactivate a neuromonitoring system, (2) high-risk surgical procedures where damage to a patient's nervous system is possible, and other problems not specifically stated herein but that may be appreciated within the field.

Figure 1:
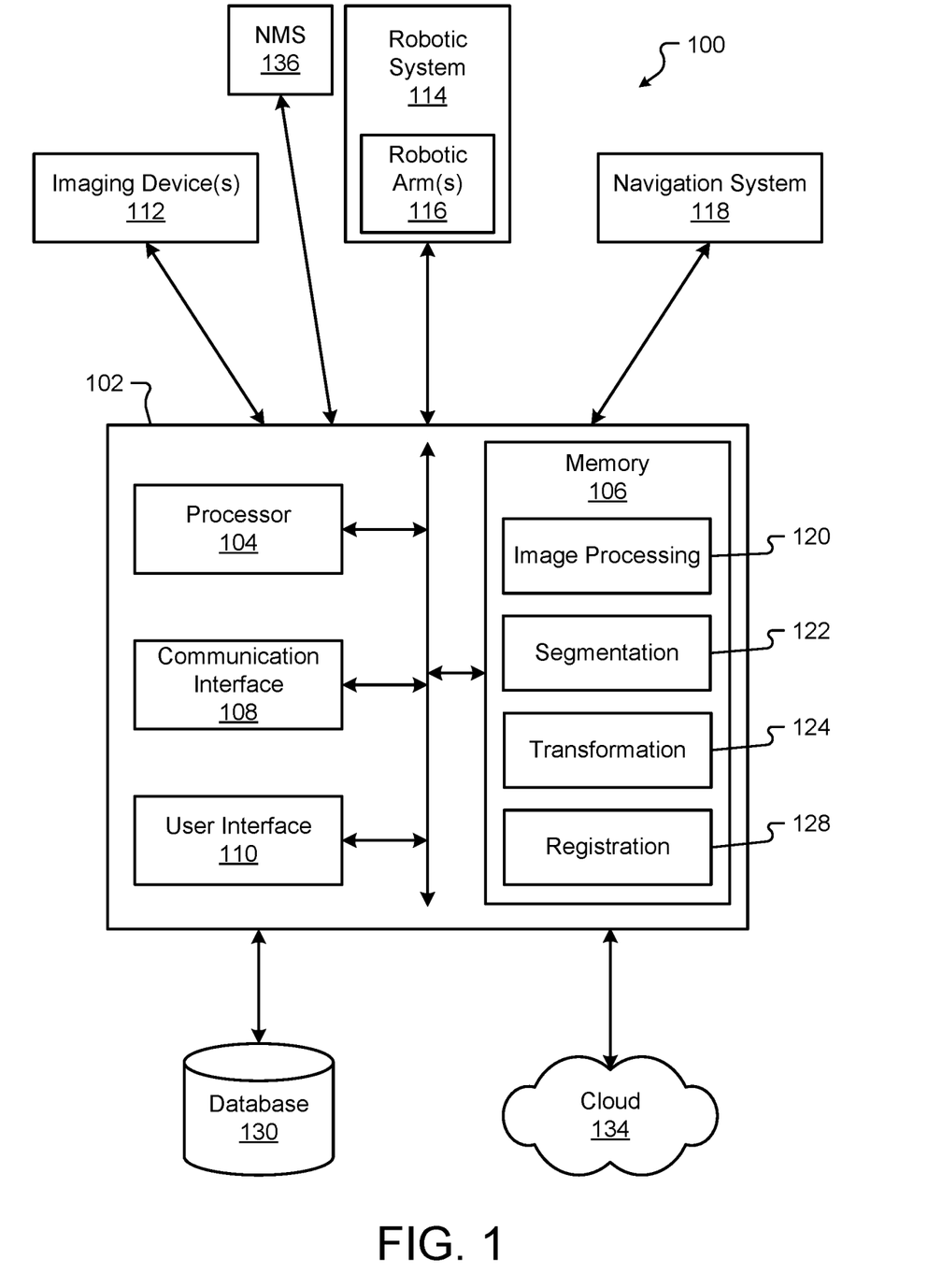
FIG. 1 is a block diagram of a system according to at least one embodiment of the present disclosure.

Turning first to FIG. 1, a block diagram of a system 100 according to at least one embodiment of the present disclosure is shown. The system 100 may be used to improve safety and/or accuracy of a surgical procedure according to one or more aspects of one or more of the methods disclosed herein. The system 100 comprises a computing device 102, one or more imaging devices 112, a robotic system 114, a navigation system 118, a database 130, a cloud or other network 134, and/or a neuromonitoring system (NMS) 136. Systems according to other embodiments of the present disclosure may comprise more or fewer components than the system 100. For example, the system 100 may not include the imaging device 112, the robotic system 114, the navigation system 118, one or more components of the computing device 102, the database 130, and/or the cloud 134.

The computing device 102 comprises processing circuitry (or a processor) 104, a memory 106, a communication interface 108, and a user interface 110. Computing devices according to other embodiments of the present disclosure may comprise more or fewer components than the computing device 102.

The processing circuitry 104 of the computing device 102 may be any processor described herein or any similar processor. The processing circuitry 104 may be configured to execute instructions stored in the memory 106, which instructions may cause the processing circuitry 104 to carry out one or more computing steps utilizing or based on data received from the imaging device 112, the robotic system 114, the navigation system 118, the database 130, the cloud 134, and/or the NMS 136. Additionally or alternatively, the processing circuitry 104 is implemented by an ASIC and/or an FPGA and/or various logic elements.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and 300 described herein, or of any other methods. The memory 106 may store, for example, instructions and/or machine learning models that support one or more functions of the robotic system 114. For instance, the memory 106 may store content (e.g., instructions and/or machine learning models) that, when executed by the processing circuitry 104, enable image processing 120, segmentation 122, transformation 124, and/or registration 128. Such content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processing circuitry 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processing circuitry 104 to manipulate data stored in the memory 106 and/or received from or via the imaging device 112, the robotic system 114, the database 130, the cloud 134, and/or the NMS 136.

The computing device 102 may also comprise a communication interface 108. The communication interface 108 may be used for receiving image data or other information from an external source (such as the imaging device 112, the robotic system 114, the navigation system 118, the database 130, the cloud 134, the NMS 136, and/or any other system or component not part of the system 100), and/or for transmitting instructions, images, or other information to an external system or device (e.g., another computing device 102, the imaging device 112, the robotic system 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processing circuitry 104 or another component of the system 100) or received by the system 100 from a source external to the system 100. In some embodiments, the user interface 110 may be useful to allow a surgeon or other user to modify instructions to be executed by the processing circuitry 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robotic system 114 may be any surgical robot or surgical robotic system. The robotic system 114 may be or comprise, for example, the Mazor X™ Stealth Edition robotic guidance system. The robotic system 114 may be configured to position the imaging device 112 at one or more precise position(s) and orientation(s), and/or to return the imaging device 112 to the same position(s) and orientation(s) at a later point in time. The robotic system 114 may additionally or alternatively be configured to manipulate a surgical tool (whether based on guidance from the navigation system 118 or not) to accomplish or to assist with a surgical task. In some embodiments, the robotic system 114 may be configured to hold and/or manipulate an anatomical element during or in connection with a surgical procedure. The robotic system 114 may comprise one or more robotic arms 116. In some embodiments, the robotic arm 116 may comprise a first robotic arm and a second robotic arm, though the robotic system 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robotic system 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robotic system 114 (or, more specifically, by the robotic arm 116) may be precisely positionable in one or more needed and specific positions and orientations.

The robotic arm(s) 116 may comprise one or more sensors that enable the processing circuitry 104 (or a processor of the robotic system 114) to determine a precise pose in space of the robotic arm (as well as any object or element held by or secured to the robotic arm).

In some embodiments, reference markers (e.g., navigation markers) may be placed on the robotic system 114 (including, e.g., on the robotic arm 116), the imaging device 112, or any other object in the surgical space. The reference markers may be tracked by the navigation system 118, and the results of the tracking may be used by the robotic system 114 and/or by an operator of the system 100 or any component thereof. In some embodiments, the navigation system 118 can be used to track other components of the system (e.g., imaging device 112) and the system can operate without the use of the robotic system 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robotic system 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robotic system 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robotic system 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The NMS 136 may include suitable hardware and/or software for monitoring one or more parameters related to a patient's nervous system (e.g., brain, spinal cord, nerves, and/or the like). In at least one non-limiting example, the NMS 136 enables intraoperative neuromonitoring of a patient's nervous system with one or more electrodes that are attached to a patient's body. The electrodes may induce and/or measure electrical signals in a manner that enables the NMS 136 monitor the state of the patient's nervous system for any unexpected or undesired changes. One or more safety precautions or safeguards may be triggered in response to unexpected or undesired readings from the NMS 136. As such, the NMS 136 may be used to enhance patient safety during a surgical procedure. In FIG. 1, the NMS 136 is shown as being coupled to the computing device 102. However, example embodiments are not limited thereto, and the NMS 136 may be in direct communication with the robotic system 114.

In related art neuromonitoring applications, a neuromonitoring device may be activated and deactivated manually during a surgical procedure. For example, a surgeon may instruct a clinician or other professional to activate neuromonitoring at specific points during the surgical procedure where the surgeon feels neuromonitoring is useful. The surgeon and/or clinician then analyzes output of the neuromonitoring device to make informed decisions about how to proceed with the surgical procedure.

As discussed in more detail below, at least one example embodiment relates to automating activation and deactivation of the NMS 136 while (optionally) automatically taking or providing additional steps for improving patient safety. For example, during a robot assisted surgical procedure, the locations of robotic arms and/or surgical tools of the robotic system may be tracked relative to sensitive parts of a patient's nervous system using the same navigation and tracking systems as described with reference to FIG. 1. The robotic system 114, having accurate knowledge of the relative locations between parts of the robotic system and parts of a patient's nervous system, may activate the NMS 136 when a part of the robotic system (e.g., a robotic arm and/or a surgical tool) comes within a threshold distance of a sensitive part of the patient, such as a nerve.

The robotic system's knowledge of the relative locations between parts of the patient and parts of the robotic system may be the result of a registration process between a coordinate system of the robotic system and a coordinate system of the patient (e.g., once the patient situated in the robotic system on an operating table). Here, the robotic system knows the relative locations of its own parts, for example, upon assembly of the robotic system. However, the robotic system may use a contour scan or other suitable scan of the patient to place the patient into the robotic system's coordinate system. Additionally or alternatively, one or more optical markers are placed on the patient to assist with accurately tracking the location of the patient within the robotic system. Meanwhile, an MR neurography image of the patient (or image from another suitable modality for identifying nerves within a patient, e.g., ultrasound) may be provided to the robotic system to enable accurate tracking of parts of the robotic system relative to parts of the patient's nervous system.

In addition to automatically activating and deactivating the NMS 136, example embodiments provide for automatically taking additional action to improve patient safety upon, during, before, or after activation of the NMS 136. For example, the system may generate one or more control signals to stop movement or operation of the robotic arm and/or surgical tool, determine and implement a new path of motion for the robotic arm and/or surgical tool, and/or produce an audio and/or visual alert for the surgeon or clinician. The robotic system may take one or more of the above actions in response to readings from the NMS 136 (e.g., the NMS 136 indicates the patient's nervous system is being negatively impacted), readings from the robotic system itself (e.g., the surgical tool is too close to a nerve), or both.

Although not explicitly illustrated, it should be appreciated that the imaging devices 112, robotic system 114, navigation system 118, database 130, cloud 134, and/or NMS 136 may include processing circuitry having the same or similar structure as the computing device 102. Additionally or alternatively, the imaging devices 112, robotic system 114, navigation system 118, database 130, cloud 134, and/or NMS 136 may be integrated with and/or controlled by the computing device 102.

Figure 2:
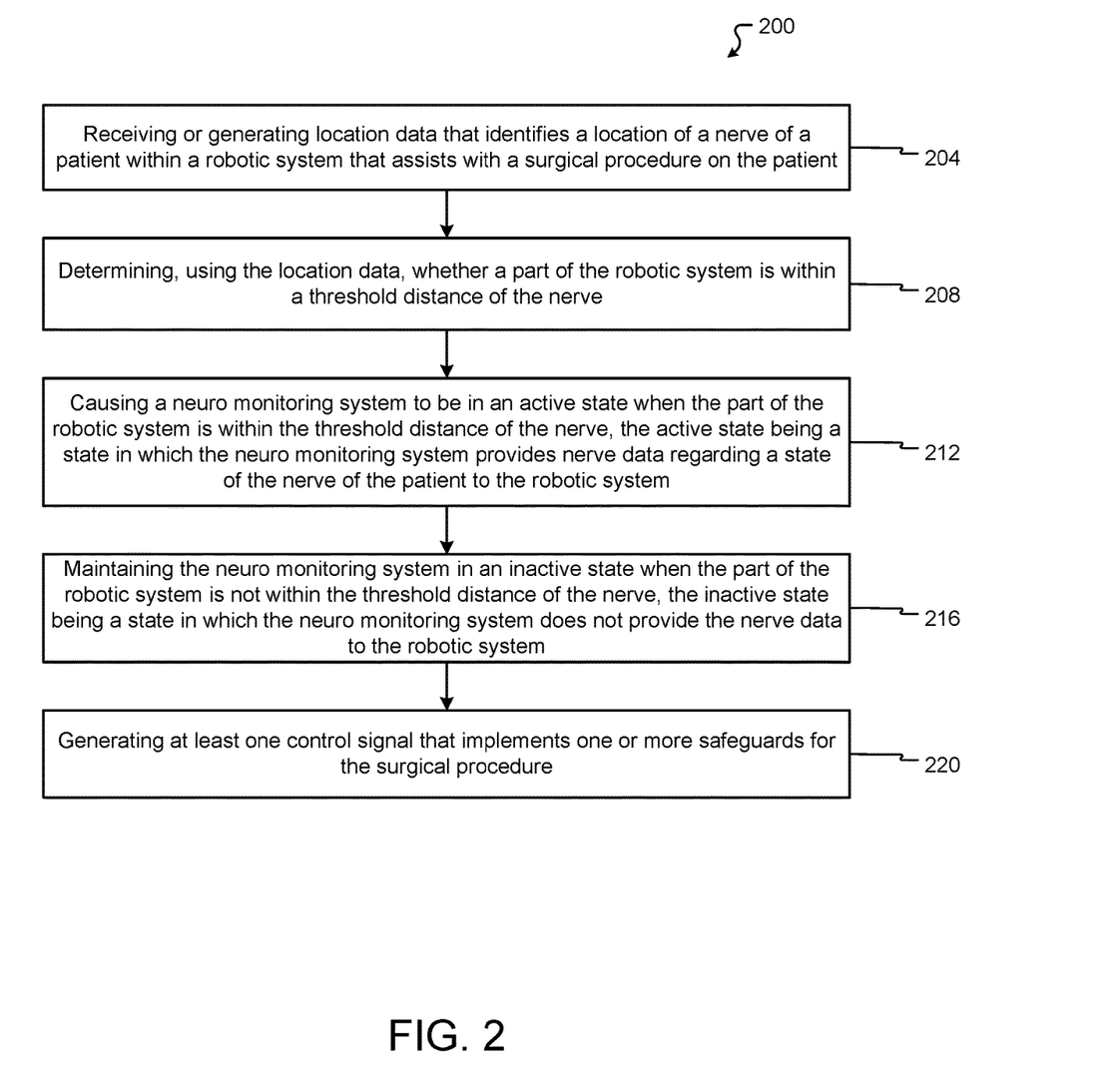
FIG. 2 is a flowchart according to at least one embodiment of the present disclosure.
Figure 3:
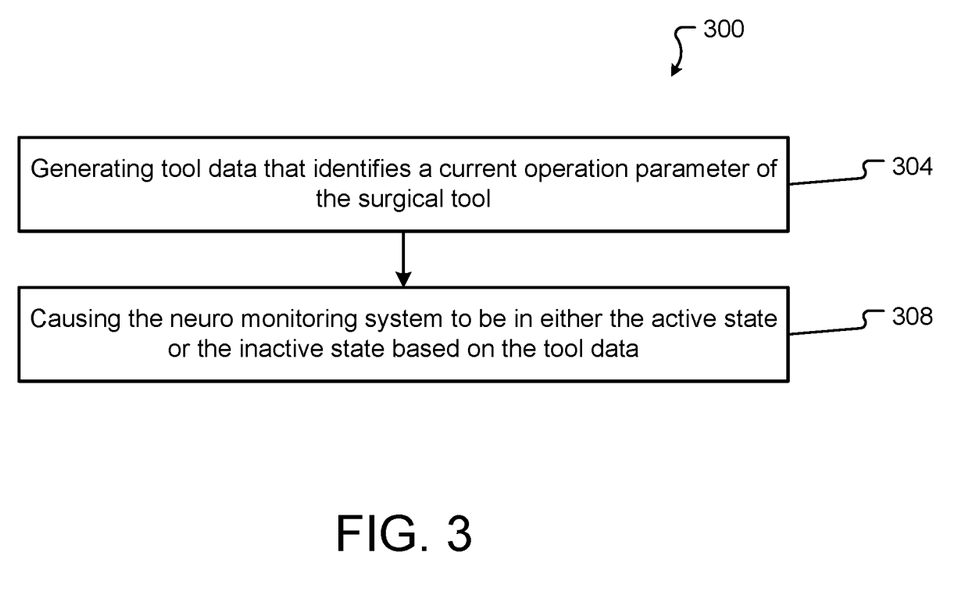
FIG. 3 is a flowchart according to at least one embodiment of the present disclosure.

The system 100 or similar systems may be used, for example, to carry out one or more aspects of any of the methods 200 and 300 described herein. The system 100 or similar systems may also be used for other purposes.

FIG. 2 depicts a method 200 that may be used, for example, to automatically activate neuromonitoring during a surgical procedure while optionally automatically implementing one or more safeguards for the surgical procedure.

The method 200 (and/or one or more steps thereof) may be carried out or otherwise performed, for example, by at least one processor. The at least one processor may be the same as or similar to the processing circuitry 104 of the computing device 102 described above. The at least one processor may be part of a robot (such as a robotic system 114) or part of a navigation system (such as a navigation system 118) or part of NMS 136. A processor other than any processor described herein may also be used to execute the method 200. The at least one processor may perform the method 200 by executing elements stored in a memory such as the memory 106. The elements stored in the memory and executed by the processor may cause the processor to execute one or more steps of a function as shown in method 200. One or more portions of a method 200 may be performed by the processor executing any of the contents of memory, such as an image processing 120, a segmentation 122, a transformation 124, and/or a registration 128.

The method 200 comprises receiving or generating location data that identifies a location of a nerve (or locations of nerves) of a patient within a robotic system 114 that assists with a surgical procedure on the patient (step 204). For example, the robotic system 114 may receive the location data from an external source (not shown) and/or generate the location data using imaging devices 112 and/or navigation system 118. As noted above, a coordinate system of the robotic system 114 and a coordinate system of the patient may be registered with one another to enable accurate tracking of parts of the robotic system 114 (e.g., robotic arms, surgical tools) relative to parts of the patient (e.g., nerves, bone, tissue, body contour, etc.). This registration process enables identification of the location of the nerve within the robotic system 114. That is, the location of the patient's nerve within a coordinate system of the robotic system 114 is known due to the registration process between the robotic system 114 and the patient (e.g., using a contour scan of the patient, a nerve scan of the patient, and/or optical markers on the patient). The location data is indicative of the location of the patient's nerve and may take any suitable form. As discussed in more detail below, example embodiments may cause the NMS 136 to be in either an active state or an inactive state based on the location data.

The method 200 also comprises determining, using the location data, whether a part of the robotic system is within a threshold distance of the nerve (step 208). For example, the robotic system 114 uses the location data regarding a location of the nerve within the coordinate system of the robotic system 114 to determine whether a part of the robotic system 114 such as a robotic arm 116, a surgical tool, and/or another part of the robotic system 114 is within the threshold distance of the nerve. As discussed in more detail below with reference to FIG. 4, the threshold distance may be defined by a boundary (e.g., a 3D boundary) around the nerve, and multiple threshold distances (and boundaries) may exist with each threshold distance being associated with triggering safety functionality. The threshold distances and boundaries may be design parameters set based on empirical evidence and/or surgeon preference.

The method 200 also comprises causing a neuromonitoring system 136 to be in an active state when the part of the robotic system 114 is within the threshold distance of the nerve (step 212). In at least one embodiment, the active state is a state in which the NMS 136 provides nerve data regarding a state of the nerve of the patient to the robotic system 114. Step 212 may include the robotic system 114 and/or the computing device 102 sending a signal to the NMS 136 to power on the NMS 136 or "wake up" the NMS 136 from a sleep mode in response to determining that part of the robotic system 114 is within the threshold distance of the nerve from step 208. Thereafter, the NMS 136 begins providing nerve data regarding measurements of the patient's nervous system, which includes measurements of the nerve from step 208. The nerve data may be provided to the robotic system 114.

The method 200 also comprises maintaining the neuromonitoring system 136 in an inactive state when the part of the robotic system 114 is not within the threshold distance of the nerve. In at least one embodiment, the inactive state is a state in which the NMS 136 does not provide the nerve data to the robotic system (step 216). For example, the NMS 136 is powered off or in a sleep mode so that data regarding the state of the patient's nervous system is not generated. Step 216 may alternatively include causing the NMS 136 to enter the inactive state if, for example, the NMS 136 was already in the active state. This scenario may correspond to a situation in which the part of the robotic system 114 within the threshold distance of the nerve moves outside the threshold distance from the nerve as a result of robotic and/or patient movement.

The method 200 also comprises generating at least one control signal that implements one or more safeguards for the surgical procedure (step 220). The at least one control signal may implement a safeguard associated with the part of the robotic system 114 determined to be within the threshold distance of the patient's nerve in step 208. For example, the at least one control signal causes movement of the robotic arm 116 to stop, causes the robotic system 114 to determine a new path of motion for the robotic arm 116 (e.g., a new path of motion that still accomplishes the same goals as the original surgical plan, or a new path of motion that belongs to an altered surgical plan, for example, if the nerve data indicates an extreme risk of damage to the nerve), causes operation of the surgical tool to stop, and/or causes an audio and/or visual alert to be produced for a professional performing or spectating the surgical procedure. Other safeguards are additionally or alternatively possible.

As may be appreciated, the at least one control signal may be generated in step 220 based on the nerve data provided by the neuromonitoring system 136 in the active state and/or based on the location data from step 204. The at least one control signal may be based on the nerve data in that the robotic system 114 implements one or more of the above safeguards when the nerve data indicates that the state of the nerve is negatively impacted or at risk of being negatively impacted. Possible states of the nerve as indicated by the nerve data include a normal state where the nerve is not damaged or not at risk of damage, a damage possible state where the nerve is at risk of damage, and a damage inflicted state where the nerve is already damaged (from the surgical procedure or not) and possibly at risk of further damage (from the surgical procedure or not). The nerve data from the NMS 136 may include raw data that needs further processing to determine the state of the nerve. Additionally or alternatively, the nerve data from the NMS 136 includes processed data that informs on the state of the nerve without further processing.

The at least one control signal generated in step 220 may be additionally or alternatively based on the location data from step 204 that identifies a location of the nerve within the coordinate system of the robotic system 114. For example, one or more of the aforementioned safeguards may be implemented even when the NMS 136 is in the inactive state so that the at least one control signal is based on only the location data. In one non-limiting example, step 220 generates the at least one control signal to cause an audio and/or visual alert when the part of the robotic system 114 moves within a second threshold distance from the nerve that is further away from the nerve that the threshold distance from step 208. The alert may inform the surgeon or other professional involved in the surgery that the part of the robotic system 114 is approaching the threshold distance from step 208 that would activate the NMS 136.

In at least one embodiment, one or more of the aforementioned safeguards may be implemented based on the location data and the nerve data. For example, the NMS 136 may be in the active state and providing the nerve data while the robotic system 114 is generating or receiving the location data. In one example scenario, the location data may be used to determine that the part of the robotic system 114 moves within a third threshold distance from the nerve that is closer to the nerve that the second threshold distance. In this case, operation 220 may include taking action based on the location data by generating at least one control signal that stops operation or movement of the part of the robotic system. At or near the same time, the NMS 136, which is already active because the part of the robotic system 114 is within the threshold distance from operation 208, is providing the nerve data about the state the nerve. At or near the same time that the location data is being consulted to generate a control signal that stops operation or movement of the robotic system 114, the concurrently provided nerve data may trigger another safeguard to determine a new path of motion or a new surgical plan for the robotic system 114 if, for example, the state of the nerve indicates a risk of damage if the current path of motion or the current surgical plan is continued.

Example embodiments are not limited to the above examples of generating control signals based on the location data or the nerve data or both the location data and the nerve data, and other examples not specifically listed herein are within the scope of inventive concepts.

The present disclosure encompasses embodiments of the method 200 that comprise more or fewer steps than those described above, one or more steps that are different than the steps described above, and/or steps performed in an order different than that discussed above.

FIG. 3 depicts a method 300 that may be used, for example, to implement an additional safeguard for a surgical procedure.

The method 300 (and/or one or more steps thereof) may be carried out or otherwise performed, for example, by at least one processor. The at least one processor may be the same as or similar to the processing circuitry 104 of the computing device 102 described above. The at least one processor may be part of a robot (such as a robotic system 114) or part of a navigation system (such as a navigation system 118) or part of NMS 136. A processor other than any processor described herein may also be used to execute the method 300. The at least one processor may perform the method 300 by executing elements stored in a memory such as the memory 106. The elements stored in memory and executed by the processor may cause the processor to execute one or more steps of a function as shown in method 300. One or more portions of a method 300 may be performed by the processor executing any of the contents of memory, such as an image processing 120, a segmentation 122, a transformation 124, and/or a registration 128.

The method 300 comprises generating tool data that identifies a current operation parameter of a surgical tool (step 304). The surgical tool may be part of the robotic system 114 (e.g., attached to a robotic arm 116). In at least one embodiment, the surgical tool is electronically powered. As such, operation parameters of the surgical tool that are monitored may include operation frequency (e.g., for a sawing tool or a drilling tool), power level, vibration induced to the patient's verve, tissue, and/or bone by the surgical tool, radiation level, and/or any suitable parameter that would be useful to monitor for the sake of improving the integrity of a patient's nervous system. In one non-limiting example, step 304 generates the tool data to identify a current operation frequency for the surgical tool.

The method 300 also comprises causing the neuromonitoring system 136 to be in either the active state or the inactive state further based on the tool data (step 308). For example, if the operation parameter being monitored exceeds or approaches a predefined limit or is outside a predefined limit range associated with increased risk of nerve damage, step 308 may cause the NMS 136 to activate and begin providing the nerve data. Else, step 308 causes or maintains the NMS 136 in the inactive state so that the NMS 136 does not provide the nerve data.

The present disclosure encompasses embodiments of the method 300 that comprise more or fewer steps than those described above, one or more steps that are different than the steps described above, and/or steps performed in an order different than that discussed above. The method 300 may be performed in addition to the method 200 or as an alternative to the method 200.

Although not explicitly illustrated as a step in FIGS. 2 and 3, it should be appreciated that at least one example embodiment enables using the nerve data and/or the location data for landmarking to map a no-fly zone for the robotic system 114. For example, activating the NMS 136 for one of the above-discussed reasons may trigger the system to log the locations on the patient at which the NMS 136 was activated and use this information to assist with modifying the current surgical plan (and/or future surgical plans) so that the robotic system 114 automatically avoids the logged locations during the surgical procedure.

As noted above, the present disclosure encompasses methods with fewer than all of the steps identified in FIGS. 2 and 3 (and the corresponding description of the methods 200 and 300, as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

Figure 4:
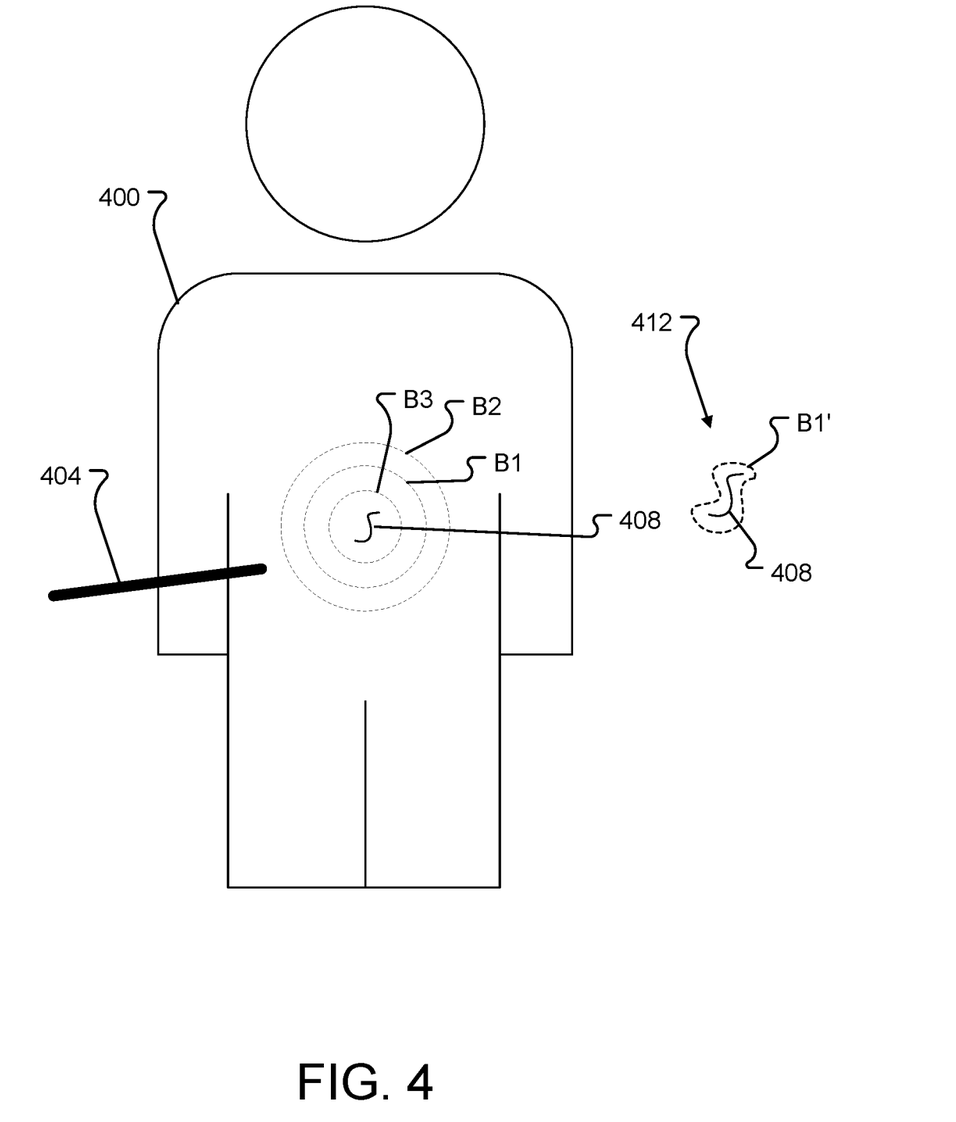
FIG. 4 is a diagram illustrating various distance thresholds with respect to a patient's nerve during a surgical procedure according to at least one embodiment of the present disclosure.

FIG. 4 illustrates various distance thresholds with respect to a patient's nerve during a surgical procedure.

As shown in FIG. 4, the patient 400 is undergoing spinal surgery that uses a surgical tool 404 (that may be attached to a robotic arm 116 of the robotic system 114, not shown). FIG. 4 further illustrates a nerve 408 or other part of the patient's 400 nervous system that is monitorable by the NMS 136. FIG. 4 further illustrates boundaries B1, B2, and B3 as dashed lines around the nerve 408. Each boundary may define one of the threshold distances discussed above with reference to FIG. 2. For example, boundary B1 defines the threshold distance from step 208 so that the surgical tool 404 crossing boundary B1 triggers activation of the NMS 136. Meanwhile, boundary B2 defines the second threshold distance that is further away from the nerve 408 than boundary B1 so that the surgical tool 404 crossing boundary B2 triggers a safeguard such as an alert that the surgical tool 404 is approaching the boundary that triggers activation of the NMS 136. Still further, boundary B3 defines the third threshold distance that is closer to the nerve 408 than boundary B1 so that the surgical tool 4040 crossing boundary B3 triggers a safeguard such as ceasing the operation of surgical tool 404.

In the example of FIG. 4, the boundaries B1, B2, and B3 are circular in nature, however, example embodiments are not limited thereto and the boundary of each threshold may be any suitable shape that could vary or stay the same for each boundary. One such example variation for a boundary is shown in graphic 412 where boundary B2' takes on the same or similar shape as the nerve 408 so that the distance from each part of the nerve 408 to the boundary of B1' is similar or substantially the same for the entire nerve 408 (additional boundaries for B2' and B3' not shown, but may also exist in the same concentrical fashion as the circular boundaries B2 and B3 but with the shape of boundary B1' so that the distance from each part of the nerve 408 to each respective boundary B2' and B3' is the similar or substantially same for the entire nerve 408).

Although three boundaries B1, B2, and B3 (or B1', B2', and B3') that define three corresponding threshold distances to the nerve 408 are shown in FIG. 4, more or fewer boundaries with associated threshold distances from the nerve 408 may exist depending on design preferences. Additionally, the shape and distance of each boundary may be a design parameter set based on empirical evidence and/or preference. In addition, it should be appreciated that the boundaries may occupy a 3D space around the entire nerve 408 (2D space depicted in FIG. 4 for ease of illustration).

Here, it should be appreciated that FIG. 4 shows boundaries for a single nerve 408, but that respective boundaries may exist for multiple nerves of the patient in or around the surgical site. The boundary or boundaries for each nerve may be formed or determined in the same or similar manner as that described for nerve 408.

As noted above, at least one example embodiment enables using the nerve data and/or the location data for landmarking to map a no-fly zone for the robotic system 114. For example, with reference to FIG. 4, the surgical tool 404 crossing one or more of the boundaries B1 to B3 and/or the NMS 136 generating nerve data for the nerve 408 that raises safety concerns at particular locations relative to the patient (whether the surgical tool 404 crosses a boundary or not) may trigger the system to log the locations at which the boundary was crossed and/or the locations at which the nerve data became concerning and use this information to assist with modifying the current surgical plan (and/or future surgical plans) so that the robotic system 114 automatically avoids the logged locations during the surgical procedure.

In at least one embodiment, aspects of the methods 200 and 300 may be combined such that any suitable combination of the tool data, location data, and nerve data are used to activate the NMS 136 and/or trigger one of the safeguards discussed above. In one non-limiting example, the NMS 136 is triggered and/or one or more safeguards are implemented when at least two of the following conditions are met: 1) the part of the robotic system 114 enters a threshold distance from a nerve; 2) the tool data indicates that the current operation data of the surgical tool 404 exceeds a limit; and 3) the nerve data indicates a sufficient risk of nerve damage.

Example embodiments have been discussed with reference to activating a specific monitoring system (e.g., NMS 136) upon a tool or other part of a robotic system crossing a predefined boundary around a nerve. However, it should be appreciated that the same or similar concepts may be applied to trigger activation of other systems used during a robotic-assisted procedure, where such other systems are for monitoring parts of a patient other than the patient's nervous system.

In view of the present disclosure, example embodiments provide improved accuracy and safety for a surgical procedure in that certain safeguards are automatically triggered based on nerve data of a nerve and/or location data of the nerve. In addition, example embodiments may reduce and/or simplify resources used during the medical procedure. For example, the role of the operator of the neuromonitoring system may be reduced or eliminated and power consumption of the overall system reduced as a result of the neuromonitoring system being activated only when necessary.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

What is claimed is:

1. A system, comprising:
  a neuromonitoring system configured to:
    monitor a nerve of a patient with one or more electrodes attached to the patient; and
    generate, based on the monitoring, nerve data regarding a state of the nerve during a surgical procedure on the patient; and
  a robotic system configured to:
    receive or generate, for the surgical procedure, location data that identifies a location of the nerve of the patient;
    cause the neuromonitoring system to be in either an active state or an inactive state based on the location data, the active state being a state in which the neuromonitoring system monitors the nerve with the one or more electrodes attached to the patient and provides corresponding nerve data to the robotic system, the inactive state being a state in which the neuromonitoring system does not monitor the nerve with the one or more electrodes and does not provide corresponding nerve data to the robotic system; and
    generate at least one control signal that implements one or more safeguards for the surgical procedure.

2. The system of claim 1, wherein the robotic system is configured to generate the at least one control signal based on the provided nerve data.

3. The system of claim 2, wherein the robotic system is configured to generate the at least one control signal further based on the location data.

4. The system of claim 1, wherein the robotic system is configured to generate the at least one control signal based on the location data.

5. The system of claim 4, wherein the robotic system further comprises:
  a robotic arm, and wherein the at least one control signal causes movement of the robotic arm to stop.

6. The system of claim 4, wherein the robotic system further comprises:
  a robotic arm, and wherein the at least one control signal causes the robotic system to determine a new path of motion for the robotic arm.

7. The system of claim 4, wherein the robotic system further comprises:
  a surgical tool, and wherein the at least one control signal causes operation of the surgical tool to stop.

8. The system of claim 1, wherein the robotic system further comprises:
  a surgical tool, wherein the robotic system is configured to:
    generate tool data that identifies a current operation frequency of the surgical tool, and
    cause the neuromonitoring system to be in either the active state or the inactive state further based on the tool data.

9. The system of claim 1, wherein the robotic system is configured to:
  determine, using the location data, whether a part of the robotic system is within a threshold distance of the nerve of the patient;
  cause the neuromonitoring system to be in the active state when the part of the robotic system is within the threshold distance of the nerve of the patient; and
  cause the neuromonitoring system to be in the inactive state when the part of the robotic system is not within the threshold distance of the nerve of the patient.

10. The system of claim 9, wherein the part of the robotic system corresponds to a robotic arm or a surgical tool.

11. The system of claim 1, wherein the at least one control signal causes an audio and/or visual alert to be produced for a clinician performing the surgical procedure.

12. A robotic system, comprising:
  a robotic arm;
  a surgical tool mechanically coupled to the robotic arm; and
  processing circuitry configured to:
    receive or generate, for a surgical procedure on a patient, location data that identifies a location of a nerve of the patient; and
    cause a neuromonitoring system to be in either an active state or an inactive state based on the location data, the active state being a state in which the neuromonitoring system monitors the nerve of the patient with one or more electrodes attached to the patient and provides corresponding nerve data regarding a state of the nerve of the patient to the robotic system, the inactive state being a state in which the neuromonitoring system does not monitor the nerve of the patient with the one or more electrodes and does not provide corresponding nerve data to the robotic system.

13. The robotic system of claim 12, wherein the processing circuitry is configured to generate at least one control signal that implements one or more safeguards for the surgical procedure.

14. The robotic system of claim 13, wherein the processing circuitry is configured to generate the at least one control signal based on the location data or the provided nerve data, or based on the location data and the provided nerve data.

15. The robotic system of claim 13, wherein the at least one control signal causes the robotic arm or the surgical tool to stop.

16. The robotic system of claim 13, wherein the at least one control signal causes the robotic arm to follow a new path of motion.

17. The robotic system of claim 12, wherein the processing circuitry is configured to:
  determine, using the location data, whether a part of the robotic system is within a threshold distance of the nerve of the patient;
  cause the neuromonitoring system to be in the active state when the part of the robotic system is within the threshold distance of the nerve of the patient; and
  cause the neuromonitoring system to be in the inactive state when the part of the robotic system is not within the threshold distance of the nerve of the patient.

18. The robotic system of claim 17, wherein the part of the robotic system corresponds to the robotic arm or the surgical tool.

19. A method, comprising:
  receiving location data that identifies a location of a nerve of a patient within a robotic system that assists with a surgical procedure on the patient;
  determining, using the location data, whether a part of the robotic system is within a threshold distance of the nerve;
  causing a neuromonitoring system to be in an active state when the part of the robotic system is within the threshold distance of the nerve, the active state being a state in which the neuromonitoring system monitors the nerve with one or more electrodes and provides corresponding nerve data regarding a state of the nerve of the patient to the robotic system; and
  maintaining the neuromonitoring system in an inactive state when the part of the robotic system is not within the threshold distance of the nerve, the inactive state being a state in which the neuromonitoring system does not monitor the nerve with the one or more electrodes and does not provide corresponding nerve data to the robotic system.

20. The method of claim 19, further comprising:
  generating, based on the nerve data provided by the neuromonitoring system in the active state, at least one control signal that implements one or more safeguards for the surgical procedure; and
  mapping a no-fly zone for the part of the robotic system based on the provided nerve data or the location data, or both of the provided nerve data and the location data.

* * * * *